United States Patent [19]

McMillan

[11] Patent Number: 4,810,632
[45] Date of Patent: Mar. 7, 1989

[54] CELL SURFACE ANTIGEN DETECTION METHOD

[75] Inventor: Robert McMillan, Del Mar, Calif.

[73] Assignee: Scripps Clinic and Research Foundation, La Jolla, Calif.

[21] Appl. No.: 936,125

[22] Filed: Dec. 1, 1986

[51] Int. Cl.[4] .................... G01N 53/00; G01N 53/564
[52] U.S. Cl. .......................................... 435/7; 435/2; 436/507; 436/518; 436/528; 436/811
[58] Field of Search ............... 435/7, 2; 436/507, 529, 436/541, 542, 811, 518, 528

[56] References Cited

U.S. PATENT DOCUMENTS 4,695,538  9/1987  Cote et al. ..................... 436/501 X

OTHER PUBLICATIONS

Woods, Jr., et al, "Autoantibodies Against Platelet . . . ", Blood 63(2), 368–375 (Feb. 1984).
Millard et al., *Blood*, 70:1495–1499 (1987).

*Primary Examiner*—Esther M. Kepplinger
*Assistant Examiner*—Richard Wagner
*Attorney, Agent, or Firm*—Dressler, Goldsmith, Shore, Sutker & Milnamow, Ltd.

[57] ABSTRACT

Chronic immune thrombocytopenic purpura is due to platelet destruction by circulating anti-platelet antibody. Although autoantibodies against the platelet glycoprotein IIb/IIIa complex and glycoprotein Ib have been demonstrated using various methods, practical assays for detection of platelet-associated or plasma autoantibodies have not been available. I studied 44 patients with chronic immune thrombocytopenic purpura where platelet-associated and plasma autoantibodies against the glycoprotein IIb/IIIa complex and glycoprotein Ib were measured using a newly developed immunobead assay and a previously reported microtiter well assay. Platelet-associated autoantibody was detected using the immunobead assay in nine of 11 patients (81.8%; seven with anti-GPIIb/IIIa, two with anti-GPIb). Plasma autoantibodies were noted in 28 of 44 patients (63.6%; 19 with anti-GPIIb/IIIa, seven with anti-GPIb and two with both). Positive results were noted in 24 of 44 patients using the immunobead assay and in only 12 of 44 using the microtiter well assay, suggesting that solubilization of the platelets prior to antibody addition, as in the microtiter well assay, alters epitope stability. Of the 20 thrombocytopenic control patients studied, all gave negative results using both assays. I conclude that these assays allow detection of autoantibodies in the majority of patients with chronic immune thrombocytopenic purpura confirming the presence of an autoimmune process. In addition, the two assays may differentiate between epitope types.

12 Claims, No Drawings

CELL SURFACE ANTIGEN DETECTION METHOD

BACKGROUND

Chronic immune thrombocytopenic purpura (ITP) is a syndrome of destructive thrombocytopenia due to an antibody against a platelet-associated antigen (1,2). Van Leeuwen et al. (3) first provided evidence that autoantibodies were present in some ITP patients. They noted that of 42 antibody eluates from ITP platelets, 32 would bind to normal but not to thrombasthenic platelets; the remaining eluates bound to both. Since thrombasthenic platelets are deficient in platelet glycoproteins (GP) IIb and IIIa, they suggested that these ITP patients had autoantibodies to one of these glycoproteins. Direct evidence for anti-glycoprotein autoantibodies in chronic ITP has been provided by subsequent studies using a variety of methods. Woods et al. showed binding of autoantibodies from ITP patients to the GPIIb-/IIIa complex or to GPIb attached to microtiter wells with monoclonal antibodies and confirmed these observations by immunoprecipitation (4,5). Using the former method, they noted anti-GPIIb/IIIa or anti-GPIb autoantibodies in about 10% of patients, much less than the percentage observed by the indirect studies of van Leeuwen et al. (3). Other investigators also detected autoantibodies in chronic ITP patients using immunoblotting (6,7), immunoprecipitation (4,5,8), inhibition of murine monoclonal anti-GPIIb/IIIa antibody binding to ITP platelets (9) and crossed immunoelectrophoresis (10). Nugent et al. (11) and Asano et al. (12) have established human hybridomas from ITP lymphocytes which synthesize monoclonal antiplatelet antibodies. Some of these are specific for platelet glycoproteins (11).

Of the arrays used for demonstrating antiglycoprotein autoantibodies in chronic ITP, the microtiter well assay (4,5) is most easily adaptable to clinical use. However, the low percentage of positive tests (about 10%) when compared to that of van Leeuwen et al. (about 76%) suggested to me that solubilization of the platelets prior to antibody sensitization may alter some of the epitopes. For this reason, I designed an assay (immunobead assay) for antiglycoprotein autoantibodies where platelets are sensitized prior to their solubilization assuming that the epitopes may remain more stable when bound to antibody. This assay can measure both platelet-associated and plasma autoantibodies. In this report, I studied 44 chronic ITP patients and noted platelet-associated autoantibodies in nine of the 11 patients studied and plasma autoantibodies in 28 of 44 patients evaluated.

BRIEF SUMMARY OF THE INVENTION

The present invention broadly contemplates a method of detecting the presence of a cell surface antigen. In accordance with this method, an aliquot of an aqueous medium suspected of containing a solubilized immunocomplex of the cell surface antigen to be detected and an antibody to an epitope of that antigen is contacted with a solid phase support capable of binding the immunocomplex to form a solid/liquid phase admixture. That admixture is maintained under biological assay conditions for a predetermined period of time, from minutes to hours such as about 30 minutes to about 2 hours, sufficient for any of the immunocomplex present to bind to the solid support. The presence of the immunocomplex is thereafter assayed for as with a labeled second antibody that immunoreacts with a second epitope of that antigen or that immunoreacts with the antibody of that immunocomplex.

As used herein, the term "solubilized immunocomplex" means a complex formed of an antibody bound to a cell surface antigen epitope whose presence is sought that is formed by reacting the antibody and cell surface antigen epitope followed by lysis the cell to form cellular debris and a solublized immunocomplex. The immunocomplex can be present in the cell sample analyzed as obtained from a patient (donor) as where the cell sample is a platelet sample from a patient with immune thrombocytopenic purpura (ITP) that contains autoantibodies to a platelet antigen such as the glycoprotein IIb/IIIa complex or glycoprotein Ib. The immunocomplex can also be formed by immunoreaction of alloantibodies of a patient with platelets or other cells of a prospective donor. The immunocomplex can still further be formed by immunoreaction of antibodies to a major histocompatibility complex (MHC) antigen epitope such as an HLA antigen epitope present on the surface of the cell.

The complex, once formed, is thereafter solublized either after or substantially simultaneously with cell lysis when the solubilized immunocomplex is formed. Cellular debris is also formed at the lysis step. Cell lysis and solubilization are conveniently carried out substantially simultaneously by contacting the cells with a detergent such as Triton X-100 [polyoxyethylene (9) octyl phenyl ether].

It is to be noted that the cell sample assayed need not contain the immunocomplex, in which case the assay for the presence of the immunocomplex will be negative. Such a negative result is particularly useful where donor/patient compatibility is of concern, or where the presence or absence of one or more MHC, HLA or other antigen epitopes is sought.

Another assay method for detecting the presence of a cell surface antigen comprises the steps of providing an aliquot of cells to be assayed. The cells of such an aliquot that bear the surface antigen to be detected have an immunocomplex that contains an antibody to the antigen sought immunoreacted with the antigen. Here, again, the immunocomplex, if present, can be present in the sample as obtained from the patient (donor) or can be prepared after obtaining the cell sample. The cells of the aliquot are lysed to provide cellular debris, and when the immunocomplex was present in the aliquot, to form a solublized immunocomplex. The presence of the solublized immunocomplex is thereafter assayed for.

In preferred practice, the cellular debris formed in the lysis/solublization step is separated from the solublized immunocomplex by any convenient means such as centrifugation. The separated, solubilized immunocomplex is thereafter affixed to a solid phase support to form a solid phase-affixed immunocomplex. The affixation can be by physical adsorption, immunoreaction using solid phase-bound antibodies directed to the antibodies of the immunocomplex, like monoclonal mouse anti-human antibodies as are available from the American Type Culture Collection of Rockville, MD (ATCC) under the accession number HB 43, or by binding with S. aureus protein A coated on the solid support. The immunocomplex is thereafter assayed for as a solid phase-affixed immunocomplex.

In one embodiment, the cells of the sample are platelets. In such an embodiment, the antibodies of the immunocomplex can be autoantibodies from the sample donor (patient) and those autoantibodies can be directed to the glycoprotein IIb/IIIa complex or glycoprotein Ib. In another embodiment, the platelets or other cells are from a first person (donor) and the antibodies of the immunocomplex can be alloantibodies from a second person (donee), as where cross-matching of platelets or other cells from a prospective donor, and serum or plasma from a patient (donee) provides the antibodies of the immunocomplex. The antibodies of the immunocomplex can also be directed to a group of cell surface antigens such as a tissue rejection-related antigen like an antigen of the MHC or an HLA antigen. Antibodies directed to an epitope present on substantially all HLA antigens as well as those directed to individual HLA-specific antigen epitopes are available from the ATCC as well as from the antiserum bank at the National Institutes of Health (NIH), Bethesda, MD.

Thus, a method is also provided for assaying platelet or other cellular compatibility between a donor and a patient (donee). In this method, an aliquot of serum or plasma from a patient suspected of having alloantibodies to a donor platelet or other cellular antigen is admixed with platelets or other cells of the donor to form an aqueous, liquid admixture. The admixture so formed is maintained under biological assay conditions for a predetermined time period sufficient for any alloantibodies present in the serum or plasma to immunoreact with the platelet or other cellular antigen to form an immunocomplex. The platelets or other cells of the admixture are lysed to form cellular debris and a solublized immunocomplex, when the alloantibodies and platelet or other cellular antigen were present in the admixture. The presence of the immunocomplex is thereafter assayed for. If the immunocomplex is not found to be present, the donor and donee are compatible, and vice versa.

The present invention also provides a method for typing cells for the presence of various surface antigens such as HLA antigens. Here an aliquot of a cell sample to be typed is reacted with an antibody that reacts with an antigen epitope common to substantially all of the group of cell surface antigens to be assayed for such as a monoclonal antibody that reacts with the backbone of the HLA antigen to form an immunocomplex. The cells are thereafter lysed to provide cellular debris and a solublized immunocomplex. The solublized immunocomplex is thereafter reacted with indicating paratopic molecules; i.e., whole antibodies or portions of antibodies that contain the paratope, that immunoreact with at least one member of the antigen group such as an HLA-specific antigen epitope to form a second immunocomplex. The presence of the second immunocomplex is then assayed for. Where HLA antigens are sought, the first-named antibodies and indicating paratopic molecules are available from the ATCC and the NIH.

Where a complete profile of cell surface antigens is desired, as where HLA typing is carried out, it is often convenient to divide the solublized immunocomplex into a plurality of aliquots. The aliquots are thereafter individually reacted with members of a panel of indicating paratopic molecules, and the presence of second immunocomplex from each of panel members is assayed for.

As used herein, the term "biological assay conditions" is used for those conditions wherein a molecule useful in this invention such as an antibody binds to another useful molecule such as an antigen epitope within a pH value range of about 5 to about 9, at ionic strengths such as that of distilled water to that of about one molar sodium chloride, and at temperatures of about 4 degrees C. to about 45 degrees C.

DETAILED DESCRIPTION OF THE INVENTION

Discussion

In this report, I describe my experience with two methods for measuring antiplatelet autoantibodies in chronic ITP: the immunobead assay which is capable of measuring both platelet-associated and plasma autoantibodies and the microtiter assay useful in detecting only plasma antibodies.

Platelet-associated autoantibodies were noted in nine of 11 ITP patients (81.8%; seven with anti-GPIIb/IIIa and two with anti-GPIb). Although the number of patients studied is too small to evaluate statistically, positive tests were seen in about the same frequency in thrombocytopenic patients studied first pre- or post-splenectomy.

Plasma autoantibodies were noted in a lesser frequency; 28/44 were positive (63.6%). Using the immunobead assay, 24/44 patients had demonstrable circulating autoantibody (18 with anti-GPIIb/IIIa and six with anti-GPIb). Fewer positive samples were noted using the microtiter assay as reported previously (4,5). Only 12/44 patients were positive using this assay (five with anti-GPIIb/IIIa, five with anti-GPIb and two with both). Three patients had autoantibodies demonstrable only with this method. This assay was positive in almost one-half of the post-splenectomy patient group (all who were refractory) while only three of the 26 patients in the pre-operative group were positive. Whether this assay predicts more severe disease or reflects the tendency of our laboratory to receive samples from more severely affected patients is not known.

These autoantibody assays have distinct advantages over assays for platelet-associated IgC (PAIgG). First, they allow the direct demonstration of either platelet-associated or plasma autoantibodies against defined platelet proteins confirming the autoimmune nature of the patient's disease. Conversely, the PAIgG assay measures IgC on platelets of unknown specificity. The adaptation of the PAIgG assay used by van Leeuwen et al. (3) where the relative binding to normal and thrombasthenic platelets is used can provide similar although indirect information in patients with anti-GPIIb/IIIa antibodies but the method is cumbersome and thrombasthenic platelets are not available to most laboratories. It is of interest that my rate of anti-GPIIb/IIIa positivity, using the combination of assays, is quite similar to theirs. Second, autoantibody test results in patients with non-immune thrombocytopenia have thus far been completely negative with these two assays while PAIgG results are positive in many patients with a variety of diagnoses (14,15). Although it seems likely, as suggested by the studies of Kelton et al. (15), that positive PAIgG results may reflect immune-mediated platelet destruction, it must be acknowledge that an increase in PAIgG does not necessarily show the presence of autoantibody. A divergence between anti-GPIIb/IIIa and PAIgG results noted in one of our ITP patients (patient 18) supports this contention. Her autoantibody values remained elevated after splenectomy despite normalization of both the platelet count and the PAIgG results. This patient subsequently relapsed, suggesting that this assay may be useful in predicting the ultimate outcome of splenectomy. Obviously these data are preliminary. Although autoantibodies were not seen in the group of thrombocytopenic control patients reported here, it seems likely that when patients with collagen vascular disease or lymphoma are screened using these assays that positive results may be seen in some of these patients groups since they have been shown to have other types of autoantibodies (e.g., anti-RBC antibodies).

The difference in the results between the immnobead and microtiter well assays is of interest. It is known from the study of purified protein antigens that there are two types of epitopes: sequential and topographic (13). Sequential epitopes involve amino acid sequences of one section of the protein while topographic epitopes involve regions of the molecule remote in sequence but close in three dimensional space due to the tertiary molecular structure. The most likely explanation for the greater percent positivity with the immunobead assay is that solubilization of the platelets prior to incubation with antibody, which is required for the microtiter assay, in some way disturbs the antigenic epitope while incubation of antibody and platelets prior to solubilization stabilizes it. I postulate that the microtiter assay measures sequential or stable topographic epitopes while the immunobead assay measures unstable topographic epitopes as well. Preliminary studies in my laboratory comparing the ability of plasma autoantibodies to precipitate the GPIIb/IIIa complex after incubation of plasma with surface-labeled platelets to that of precipitating radiolabeled purified GPIIb/IIIa support this hypothesis. Plasmas positive in both the microtiter and immunobead assays (three studied) are capable of precipitating both the purified GPIIb/IIIa complex and the complex from surface-labeled platelets while plasmas positive in the immunobead but negative in the microtiter assay (four studied) are able to precipitate only the complex from surface-labeled platelets. Obviously, further studies will be needed to confirm these preliminary findings.

These assays are both adaptable to the measurement of other as yet unidentified autoantibodies when appropriate monoclonal antibodies become available. Since many patients with chronic ITP have no demonstrable autoantibody, it seems likely that autoantibodies against other platelet-associated antigens (e.g., phospholipids, glycolipids, etc.) are present.

In summary, the present studies describe the use of two assays for the measurement of autoantibodies to specific platelet proteins. Results show that the majority of patients with chronic ITP have autoantibodies against either the platelet GPIIb/IIIa complex or against GPIb. Differences in the frequency of positive results seen in the two assays provide evidence for epitopes which have varying degrees of stability upon solubilization.

Results

Chronic ITP Patients

The results were divided into two groups for evaluation: (1) presplenectomy patients—the initial study sample was obtained prior to splenectomy although in some of these patients additional studies were also performed after surgery; (2) post-splenectomy patients—the patient was first studied after surgery.

Pre-splenectomy studies (Table 1)

TABLE 1

ANTI-PLATELET GLYCOPROTEIN AUTOANTIBODIES
PRE-SPLENECTOMY CHRONIC ITP PATIENTS

| Patient | Platelet Count (per mm³) | Splx | Resp | PAIgG | Anti-GPIIb/IIIa Immunobead P-Assoc | Anti-GPIIb/IIIa Immunobead Plasma | Anti-GPIIb/IIIa Well | Anti-GPIb Immunobead P-Assoc | Anti-GPIb Immunobead Plasma | Anti-GPIb Well |
|---|---|---|---|---|---|---|---|---|---|---|
| 1 | 2000 | Yes | ? | — | 16.7 | 2.3 | Neg | — | 0.8 | Neg |
| 2 | 9000 | Yes | CR | — | — | 0.8 | Neg | — | 1.0 | Neg |
| 3 | 9000 | Yes | CR | — | — | 0.9 | Neg | — | 0.9 | Neg |
| 4 | 9000 | Yes | NR | — | — | 4.5 | Neg | — | 0.9 | Neg |
| 5 | 10000 | No | — | — | — | 0.9 | Pos (320) | — | 1.0 | Pos (80) |
| 6 | 14000 | Yes | NR | — | — | 1.5 | Neg | — | 1.1 | Neg |
| 7 | 18000 | Yes | CR | 12962 | — | 0.6 | Neg | — | 1.0 | Neg |
| 8 | 19000 | No | — | 4423 | — | 1.4 | Neg | — | 0.9 | Neg |
| 9 | 20000 | No | — | 4873 | — | 1.3 | Neg | — | 0.9 | Neg |
| 10 | 23000 | Yes | CR | — | — | 1.7 | Neg | — | — | Neg |
| 11 | 34000 | Yes | CR | 7353 | — | 1.6 | Neg | — | — | Neg |
| 12 | 39000 | No | — | 30990 | — | 0.9 | Neg | — | 2.0 | Neg |
| 13 | 40000 | Yes | NR | 3453 | — | 1.0 | Neg | — | 0.9 | Neg |
| 14 | 40000 | Yes | NR | — | 30.1 | 5.5 | Neg | — | 1.1 | Neg |
| 15 | 42000 | No | — | — | 0.6 | 0.7 | Neg | 1.0 | 1.2 | Neg |
| 16 | 46000 | No | — | 9036 | — | 1.1 | Neg | — | 0.8 | Neg |
| 17 | 50000 | Yes | NR | 11049 | — | 0.9 | Neg | — | 0.9 | Neg |
| 18 | 50000 | Yes | NR | 17143 | 16.1 | 3.9 | Neg | — | 0.8 | Neg |
| 19 | 50000 | No | — | — | 10.0 | 2.5 | Neg | — | 0.8 | Neg |
| 20 | 69000 | No | — | 7286 | 0.7 | 0.6 | Neg | 4.9 | 1.8 | Neg |
| 21 | 85000 | Yes | CR | 1351 | — | 1.2 | Pos (640) | — | — | Neg |
| 22 | 100000 | No | — | — | — | 0.9 | Neg | — | 1.2 | Neg |
| 23 | 106000 | Yes | CR | 5152 | 16.2 | 1.4 | Neg | — | — | Neg |
| 24 | 112000 | No | — | 3537 | — | 0.9 | Neg | — | 3.6 | Pos (40) |
| 25 | 145000 | Yes | ? | 3692 | — | 3.1 | Neg | — | 1.1 | Neg |
| 26 | 261000 | Yes | CR | 3075 | — | 0.8 | Neg | — | 1.2 | Neg |

Splx - splenectomy; Resp-response: CR - normalization of platelet count; NR - no response or relapse after an initial response or ? if lost to followup; PAIgG - platelet-associated IgG (ng/$10^9$ plts); Immunobead - results of platelet-associated (P-Assoc) or Plasma immunobead assay expressed as a ratio of patient/control results (positive > 1.3); well - results of microtiter well asssy expressed as negative (neg) or positive (pos) with titers of positive tests shown in parenthesis.

Twenty-six patients were studied; 16 subsequently had their spleens removed and eight entered a complete remission, six were splenectomy failures and two were lost to followup. Platelet-associated autoantibody was measured using the immunobead assay in seven of the 26 patients. Of these, six (85.7%) were positive with ratios ranging from 4.9 to 30.1 (control values <1.3); five had anti-GPIIb/IIIa and one had anti-GPIb autoantibodies.

Platelet-associated autoantibodies in three of these patients (patients 14, 18 and 23) were also studied after splenectomy (Table 2). In the patient who attained a complete remission (patient 23), the anti-GPIIb/IIIa autoantibodies present prior to splenectomy were no longer demonstrable after surgery. In the two others, the autoantibodies persisted despite splenectomy and although both obtained a temporary increase in the platelet count after surgery (135,000/mm$^3$ in one and 313,000/mm$^3$ in the other), they both became severely thrombocytopenic (<20,000) within a few weeks after surgery. Table 2 also compares the platelet-associated IgG (PAIgG) and the platelet-associated anti-GPIIb/IIIa values prior to and after splenectomy. In patient 23, who attained a complete remission, and patient 14, who responded only partially, the values of both determinations varied concordantly. However, in patient 18 whose platelet count became normal briefly after surgery but who later relapsed (platelet count 14,000/mm$^3$), the PAIgG values became normal in concert with the platelet count but the platelet-associated anti-GPIIb/IIIa remained elevated.

TABLE 2

THE EFFECT OF SPLENECTOMY ON ANTI-GPIIb/IIIa AUTOANTIBODY AND PLATELET-ASSOCIATED IgG

| Patient | Sample* Day | Therapy | Platelet Count (per mm$^3$) | Anti-GPIIb/IIIa (Ratio) | PAIgG (ng per 10$^9$ plts) |
|---|---|---|---|---|---|
| 14 | −25 | P | 40,000 | 28.8 | 8,900 |
|    | 0 | P | 96,000 | 21.2 | 5,847 |
|    | +5 | — | 135,000 | 25.4 | 6,595 |
|    | +52 | — | 109,000 | 31.1 | 19,500 |
| 18 | −111 | — | 51,000 | — | 17,140 |
|    | 0 | P | 118,000 | 16.1 | 4,400 |
|    | +5 | — | 103,000 | 13.7 | 4,394 |
|    | +8 | — | 313,000 | 11.3 | 2,611 |
| 23 | −1 | P | 106,000 | 16.2 | 5,152 |
|    | +28 | — | 465,000 | 1.0 | 985 |
| Control | | | 180–400,000 | <1.3 | <3300 |

TABLE 2-continued

THE EFFECT OF SPLENECTOMY ON ANTI-GPIIb/IIIa AUTOANTIBODY AND PLATELET-ASSOCIATED IgG

| Patient | Sample* Day | Therapy | Platelet Count (per mm$^3$) | Anti-GPIIb/IIIa (Ratio) | PAIgG (ng per 10$^9$ plts) |
|---|---|---|---|---|---|
| Values | | | | | |

Anti-GPIIb/IIIa - platelet-associated autoantibodies against the platelet glycoprotein IIb/IIIa complex measured by the immunobead assay.
PAIgG - platelet-associated IgG
P - high dose prednisone
*Number of days before (—) or after splenectomy; day 0 is the day of surgery.

Plasma autoantibodies were studied in all patients using both assays; 16/26 (81.5%) were positive in at least one of the assays. Eleven had circulating anti-GPIIb/IIIa and three had anti-GPIb autoantibodies when studied using the immunobead assay; ratios varied from 1.4 to 5.5. Of these patients with positive immunobead assays, only one (patient 24) was also positive using the microtiter assay. Two patients with negative immunobead assays (patients 5 and 21) were positive using the microtiter assay; one of these (patient 5) had antibody in the microtiter assay to both GPIIb/IIIa and GPIb.

Post-splenectomy Studies (Table 3)

All patients in this group failed to maintain a normal platelet count after splenectomy. Platelet-associated autoantibody was measured using the immunobead assay in four of the 18 patients in this group. Three were positive, one with autoantibodies against GPIIb/IIIa and the other two against GPIb.

Plasma autoantibodies were demonstrable using the immunobead assay in ten of the 18 patients (55%), seven with anti-GPIIb/IIIa and three with anti-GPIb. Seven of the ten patients with positive immunobead assays also had autoantibodies of the same specificity shown by the microtiter assay. Two patients (patients 9 and 12) were positive in the microtiter assay but negative by the immunobead method. One patient (patient 4) had autoantibodies against both antigens.

Thrombocytopenic Controls

Platelets (eight patients) and plasma (20 patients) from patients with non-immune thrombocytopenia were studied using both assays. Negative results were obtained in every instance using both the immunobead and the microtiter assays (data not shown).

TABLE 3

ANTI-PLATELET GLYCOPROTEIN AUTOANTIBODIES POST-SPLENECTOMY CHRONIC ITP PATIENTS

| Patient | Platelet Count (per mm$^3$) | PAIgG | Anti-GPIIb/IIIa Immunobead P-Assoc | Anti-GPIIb/IIIa Immunobead Plasma | Anti-GPIIb/IIIa Well | Anti-GPIb Immunobead P-Assoc | Anti-GPIb Immunobead Plasma | Anti-GPIb Well |
|---|---|---|---|---|---|---|---|---|
| 27 | 1000 | — | — | — | Neg | — | 3.3* | Pos (6400) |
| 28 | 3000 | — | — | 2.2 | — | Neg | ( ) | Neg |
| 29 | 3000 | 6911 | — | 1.0 | Neg | — | 1.0 | Neg |
| 30 | 3000 | 59800 | — | 1.3 | Pos (40) | — | 2.6 | Pos (80) |
| 31 | 6000 | — | 7.0** | 9.4 | Pos (640) | — | 1.2 | Neg |
| 32 | 6000 | — | — | 0.9 | Neg | — | 0.9 | Neg |
| 33 | 7000 | 53000 | — | 5.2 | Pos (320) | — | 0.9 | Neg |
| 34 | 7000 | — | — | 1.2 | Neg | 17.2 | 2.0 | Pos (20) |
| 35 | 9000 | — | — | 0.6 | Neg | 1.0 | 0.9 | Pos (40) |
| 36 | 9000 | — | — | 1.0 | Neg | — | 1.1 | Neg |
| 37 | 13000 | — | — | 2.5 | Neg | — | 0.9 | Neg |
| 38 | 14000 | — | 0.6 | 0.7 | Neg | 5.7 | 1.3 | Pos (80) |
| 39 | 21000 | 42396 | — | 3.8 | Neg | — | 0.8 | Neg |
| 40 | 24000 | 6326 | — | 0.9 | Neg | — | 1.1 | Neg |
| 41 | 34000 | — | — | 0.6 | Neg | — | 1.0 | Neg |
| 42 | 40000 | 5650 | — | 2.6 | Neg | — | 1.1 | Neg |
| 43 | 42000 | 19024 | — | 1.0 | Neg | — | 0.9 | Neg |

TABLE 3-continued
ANTI-PLATELET GLYCOPROTEIN AUTOANTIBODIES POST-SPLENECTOMY CHRONIC ITP PATIENTS

| Patient | Platelet Count (per mm³) | PAIgG | Anti-GPIIb/IIIa | | | Anti-GPIb | | |
|---|---|---|---|---|---|---|---|---|
| | | | Immunobead | | | Immunobead | | |
| | | | P-Assoc | Plasma | Well | P-Assoc | Plasma | Well |
| 44 | 117000 | 11795 | — | 2.1 | Pos (40) | — | 1.1 | Neg |

PAIgG - platelet-associated IgG (ng/10⁹ plts); immunobead - results of platelet-associated (P-Assoc) or plasma immunobead assay expressed as a ratio of patient/control results (positive >1.3); well - results of the microtiter well assay expressed as negative (neg) or positive (pos) with titers of positive tests shown in parenthesis.
*0.1 ml of plasma used to sensitize platelets.
**0.18 × 10⁸ platelets assayed.

MATERIALS AND METHODS

Studies

I studied plasma or platelet samples obtained between Jan. 1, 1982 and July 1, 1986 from 44 patients with chronic ITP, 20 control subjects and 20 thrombocytopenic controls (acute non-lymphocytic leukemia, 3 patients; acute lymphoblastic leukemia, 2 patients; bone marrow transplantation patients with anti-HLA antibodies, 3 patients; aplastic anemia, 2 patients; nonHodgkins lymphoma, 3 patients (one with cryoglobulins); cirrhosis, one patient; myeloproliferative disease, 3 patients; and carcinoma on chemotherapy, 3 patients). Patients with ITP were thrombocytopenic with normal or increased numbers of megakaryocytes and without evidence of other types of immune thrombocytopenia.

Assays for Antiglycoprotein Autoantibody

The specificity of both the immunobead and microtiter assays is determined by the monoclonal antiglycoprotein antibody employed. The following murine monoclonal antibodies were used: anti-GPIIb/IIIa-2A9, 3F5, 2G12 (provided by Dr. V. L. Woods)—2A9 is specific for GPIIb and the others are complex-specific; anti-GIb-P3 (provided by Drs. Zaverio Ruggeri and Theodore Zimmerman, Scripps Clinic); and antihuman IgG (American Type Culture Collection. Rockville, MD. ATCC HB-43). Monoclonal antibodies (50 $\mu$g) were labeled with 500 $\mu$Ci of $^{125}$I using the chloramine-T method. All incubations in both assays were carried out at room temperature.

It is known that in detergent extracts GPIIb and GPIIIa form a complex and that GPIb is complexed with platelet glycoproteins IX and V. Therefore, as measured by these two assays, anti-GPIIb/IIIa autoantibodies could be against epitopes on either GPIIb or GPIIIa and anti-GPIb specific for GPIb, GP V or CP IX. However, for the purposes of this report, results will be reported as either anti-GPIIb/IIIa or anti-GPIb referring to autoantibodies against proteins of the GPIIb/IIIa complex or the GPIb complex.

Immunobead Assay

This assay can be used to measure either platelet-associated autoantibody or plasma autoantibody.

Immunobead Preparation

Anti-IgG-coated immunobeads were prepared by incubating polystyrene beads (Poly-Sep, Polysciences Inc., Warrington, PA) with murine monoclonal antihuman IgC (ATCC HB-43) in saline for 60 min at a bead/antibody ratio of 2000:1 by weight (e.g., 100 mg of beads to 50 $\mu$g of anti-IgC in 2 ml of saline). The beads were then centrifuged for 10 sec at maximum speed in a tabletop centrifuge (International Clinical Centrifuge, Model 54133M). After washing once with 10 ml of 0.05% Tween-20 in phosphate-buffered saline, pH 7.4 (PBS-Tween), nonspecific binding sites are blocked by incubation of the beads in 2% bovine serum albumin (BSA) in PBS-Tween for 60 min followed by four washes in PBS-Tween.

Platelet Preparation

Platelets from EDTA-anticoagulated blood were obtained from the patient or from a normal donor and washed six times with 0.05M isotonic citrate buffer. To prepare antibody-sensitized platelets, washed normal platelets ($10^8$ in 0.1 ml) were incubated with 1.0 ml of patient or control plasma. containing PGE$_1$ (1 $\mu$g/ml) and theophylline (1 $\mu$M), for 60 min at room temperature and then washed four times with 0.05M citrate buffer containing PGE$_1$ and theophylline. Patient platelets ($10^8$) or the antibody-sensitized platelets were resuspended in 900 $\mu$l of citrate buffer containing leupeptin (100 $\mu$g/ml) and then solubilized by adding 100 $\mu$l of 10% Triton X-100. Control samples were handled similarly.

Assay

The solubilized platelets from each sample were centrifuged at 12,000 xg for 5 min. Preliminary studies showed that this step was required, particularly in anti-GPIb autoantibody studies, to prevent falsely elevated values. The supernate is then incubated for 60 min with 100 mg of anti-IgG-coated immunobeads to allow attachment of IgG and any bound antigen. After four washes with PBS-Tween, the presence of specific antigen is demonstrated by incubating the beads with 1.0 ml of PBS-Tween containing about 400,000 cpm of $^{125}$I monoclonal antibody specific for either anti-GPIIb/IIIa (a cocktail of 3 monoclonal antibodies specific for non-competing sites, 2A9, 3F5, and 2G12) or anti-GPIb (P3) for 60 min at room temperature and then washing four times with PBS-Tween. The beads were resuspended in 1 ml of buffer and 0.5 ml was removed for determining radioactivity. Data are expressed as a binding ratio of cpm of patient sample/mean cpm of three control samples. The mean percent variation results of replicate samples of control platelets and platelets sensitized with control plasma were: anti-GPIIb/IIIa-10.1±7.5 (14 studies) and 9.1±8.1 (31 studies), respectively, and anti-GPIb-6.8±7.0 (17 studies) and 7.9±7.6 (24 studies), respectively. Patient samples with a binding ratio of >1.3 are considered positive (>2 S.D. over control). Preliminary studies show that positive reactivity can be removed by adsorption of plasma with excess platelets. In addition, storage of samples for up to four days at 4° C. did not affect platelet or plasma control values.

Microtiter Well Assay

Details have been previously published (4,5). Briefly, washed platelets ($10^9$ ml) or CEM leukemic cells ($10^7$ ml) in PBS containing leupeptin (100 $\mu$g/ml) were solubilized in 1% Triton X-100 for 30 min at 4° C. and then ultracentrifuged (100,000 xg for 60 min). The lysates are stored at −70° C. Microtiter wells are coated overnight at 5° C. with 100 $\mu$l of either anti-GPIIb/IIIa (2A9 or 3F5) or anti-GPIb (P3) at a concentration of 5 μg/ml. After six washes with 200 μl of PBS-Tween, the remaining binding sites were blocked for 60 min with 200 μl of 2% BSA in PBS-Tween. After six washes with PBS-Tween, 100 μl of platelet lysate or the antigen negative CEM lysate, diluted 1:10, were added and incubated for 60 min. This allows attachment of the specific platelet antigen to the well-bound monoclonal antibody. After six washes, appropriate dilutions (1:10 for screening plasma and higher dilutions if positive) of patient or control plasma were added and incubated for 60 min. After six washes, 100 μl of radiolabeled murine monoclonal antihuman IgG (about 100,000 cpm) were added and after 60 min incubation and six final washes, the radioactivity of each well was determined. The percent variation for replicate control plasmas is $-50\pm7.7$ for anti-GPIIb/IIIa and $-1.9\pm6.4$ for anti-GPIb (4,5). Samples with a percent increase of >11 were considered positive (>2 S.D.).

REFERENCES

1. McMillan R: Chronic idiopathic thrombocytopenic purpura. N Engl J Med 304: 1135–1147, 1981
2. Kelton J G, Gibbons S: Autoimmune platelet destruction: Idiopathic thrombocytopenic purpura. Semin Thromb Haemost 8: 83–104, 1982
3. van Leeuwen E F, van der Ven J T H, Engelfriet CP et al: Specificity of autoantibodies in autoimmune thrombocytopenia. Blood 59: 23–26, 1982
4. Woods V L, Oh E H, Mason D et al: Autoantibodies against the platelet glycoprotein IIb/IIIa complex in patients with chronic ITP. Blood 63: 368–375, 1984
5. Woods V L, Kurata Y, Montgomery R R et al: Autoantibodies against platelet glycoprotein Ib in patients with chronic idiopathic thrombocytopenic purpura. Blood 64: 156–160, 1984
6. Mason D, McMillan R: Platelet antigens in chronic idiopathic thrombocytopenic purpura. Br J Haematol 56: 529–534, 1984
7. Beardsley D S, Spiegel J E, Jacobs M M et al: Platelet membrane glycoprotein IIIa contains target antigens that bind antiplatelet antibodies in immune thrombocytopenia. J Clin Invest 74: 1701–1707, 1984
8. Devine D V, Rosse W F: Identification of platelet proteins that bind alloantibodies and autoantibodies. Blood 64: 1240–1245, 1984
9. Varon D, Karpatkin S: A monoclonal antiplatelet antibody with decreased reactivity for autoimmune thrombocytopenic platelets. Proc Natl Acad Sci USA 80: 6992–6995, 1983
10. Szatkowski N S, Kunicki T J, Aster R H: Identification of glyprotein Ib as a target for autoantibody in idiopathic (autoimmune) thrombocytopenic purpura. Blood 67: 310–315, 1986
11. Nugent D J, Berglund C, Bernstein I D: Isolation of platelet-specific human monoclonal antibodies using Epstein-Burr virus transformation and somatic cell hybridization. Proceedings of the INSERM Symposium on utilization of monoclonal antibodies for the understanding and detection of platelet activity. Amsterdam, Elsevier Science Publishers, 1986
12. Asano T, Furie B C, Furie B: Platelet binding properties of monoclonal lupus autoantibodies produced by human hybridomas. Blood 66: 1254–1260, 1985
13. Berzofsky J A: Intrinsic and extrinsic factors in protein antigenic structure. Science 229: 932–940, 1985
14. Mueller-Eckhardt C, Mueller-Eckhardt G, Kayser W et al: Platelet-associated IgG, platelet survival, and platelet sequestration in thrombocytopenic states. Br J Haematol 52: 49–58, 1982
15. Kelton J G, Powers P J, Carter C J: A prospective study of the usefulness of the measurement of platelet-associated IgG for the diagnosis of idiopathic thrombocytopenic purpura. Blood 60: 1050–1053, 1982

What is claimed is:

1. A method of detecting the presence of a cell surface antigen comprising:
   (a) contacting an aliquot of an aqueous medium suspected of containing a solubilized immunocomplex of the cell surface antigen to be detected and an antibody to an epitope of said antigen with a solid support capable of binding said solubilized immunocomplex to form a solid/liquid phase admixture, said solubilized immunocomplex formed by lysing cells suspected of containing said immunocomplex and solubilizing the cell lysate;
   (b) maintaining said solid/liquid phase admixture under biological assay conditions for a predetermined time period sufficient for any of said solubilized immunocomplex present to bind to said solid support; and
   (c) assaying for the presence of said immunocomplex bound to said solid support.

2. A method of detecting the presence of a cell surface antigen comprising the steps of:
   (a) providing an aliquot of cells to be assayed, the cells of said aliquot bearing the surface antigen to be detected and suspected of having an immunocomplex containing an antibody to said antigen immunoreacted with said antigen;
   (b) lysing the cells of said aliquot to provide cellular debris, and, when said immunocomplex was present in the aliquot, a solubilized immunocomplex; and
   (c) assaying for the presence of said immunocomplex.

3. The method of claim 2 wherein the cells of said aliquot are platelets.

4. The method of claim 3 wherein said antibodies of said immunocomlex are autoantibodies.

5. The method of claim 4 wherein said autoantibodies are directed to the platelet glycoprotein IIb/IIIa complex or glycoprotein Ib.

6. The method of claim 3 wherein said platelets are from a first person and said antibodies are alloantibodies from a second person.

7. The method of claim 3 wherein the antibodies of said immunocomplex are directed to a major histocompatibility complex antigen.

8. The method of claim 7 wherein the major histocompatibility complex antigen is an HLA antigen.

9. The method of claim 2 further including the steps of:
   (i) separating the cellular debris from any solubilized immunocomplex present in step (b);
   (ii) affixing any of said separated, solubilized immunocomplex present to a solid phase support to form a solid phase-affixed immunocomplex; and
   (iii) thereafter, assaying for the presence of said immunocomplex as a solid phase-affixed immunocomplex.

10. A method of assaying platelet compatibility between donor and patient comprising the steps of:

(a) admixing an aliquot of serum or plasma from a patient suspected of having alloantibodies to a donor platelet antigen with platelets of a prospective donor to form an aqueous, liquid admixture;

(b) maintaining said admixture under biological assay conditions for a predetermined time period sufficient for any alloantibodies present in the serum or plasma to immunoreact with the platelet antigen to form a platelet antigen-alloantibody immunocomplex;

(c) lysing the platelets of said admixture to form cellular debris and a solublilized platelet antigen-alloantibody immunocomplex when said alloantibodies and said platelet antigen were present in said admixture; and (d) assaying for the presence of said platelet antigen-alloantibody immunocomplex.

11. A method of typing cells for the presence of a group of cell surface antigens comprising the steps of:

(a) reacting an aliquot of a cell sample to be typed with antibodies that react with an antigen epitope common to substantially all of the group of the cell surface antigens sought to form a common epitope-antibody immunocomplex;

(b) lysing the cells of said sample to provide cellular debris and a solubilized common epitope-antibody immunocomplex;

(c) reacting the solubilized common epitope-antibody immunocomplex with indicating paratopic molecules that immunoreact with at least one specific cell surface antigen epitope of the group of cell surface antigens to form a second immunocomplex; and (d) assaying for the presence of said second immunocomplex.

12. The method of claim 11 wherein said said group of cell surface antigens are the HLA antigens.

* * * * *

UNITED STATES PATENT AND TRADEMARK OFFICE
CERTIFICATE OF CORRECTION

PATENT NO. : 4,810,632

DATED : March 7, 1989

INVENTOR(S) : Robert McMillan

It is certified that error appears in the above-identified patent and that said Letters Patent is hereby corrected as shown below:

Column 1, line 4, after the heading "BACKGROUND", insert the following paragraph:

--This invention was made with government support under Contract AM 16125 awarded by the National Institutes of Health. The government has certain rights in the invention.--

Signed and Sealed this

Twenty-fifth Day of January, 1994

Attest:

BRUCE LEHMAN

*Attesting Officer*    *Commissioner of Patents and Trademarks*